US011051801B2

(12) United States Patent
Roorda et al.

(10) Patent No.: US 11,051,801 B2
(45) Date of Patent: *Jul. 6, 2021

(54) CLOSURE DEVICES AND METHODS

(71) Applicant: Abbott Cardiovascular Systems, Inc., Santa Clara, CA (US)

(72) Inventors: Wouter E. Roorda, Palo Alto, CA (US); Douglas H. Mehl, Redwood City, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 252 days.

This patent is subject to a terminal disclaimer.

(21) Appl. No.: 16/353,648

(22) Filed: Mar. 14, 2019

(65) Prior Publication Data
US 2019/0209162 A1    Jul. 11, 2019

Related U.S. Application Data

(63) Continuation of application No. 15/149,805, filed on May 9, 2016, now Pat. No. 10,271,834, which is a
(Continued)

(51) Int. Cl.
*A61B 17/04* (2006.01)
*A61B 17/06* (2006.01)
*A61B 17/00* (2006.01)

(52) U.S. Cl.
CPC ...... *A61B 17/0469* (2013.01); *A61B 17/0057* (2013.01); *A61B 17/0482* (2013.01);
(Continued)

(58) Field of Classification Search
CPC ............ A61B 17/0469; A61B 17/0057; A61B 17/06004; A61B 17/0482;
(Continued)

(56) References Cited

U.S. PATENT DOCUMENTS 5,700,273 A * 12/1997 Buelna .................. A61B 17/04
606/144
5,830,125 A   11/1998 Scribner et al.
(Continued)

OTHER PUBLICATIONS

U.S. Appl. No. 13/111,576, filed Apr. 4, 2014, Office Action.
(Continued)

*Primary Examiner* — Jocelin C Tanner
(74) *Attorney, Agent, or Firm* — Workman Nydegger; Randy Shen

(57) ABSTRACT

A closure device for closing an opening in tissue is provided. The closure device includes an elongate member through which needles may be deployed. The closure device also includes a closure element having a foot portion and a needle guide portion. The foot portion and the needle guide portion are each movable between a delivery configuration and a deployed configuration. The foot portion includes cuffs removably mounted thereon and having sutures connected therebetween. The needle guide portion includes needle guide apertures that guide the needles to the cuffs. The needles securely engage the cuffs and draw the cuffs and suture through the lumen wall so that the opening in the lumen wall can be closed with the sutures.

19 Claims, 14 Drawing Sheets

Related U.S. Application Data continuation of application No. 13/111,576, filed on May 19, 2011, now Pat. No. 9,332,981.

(52) U.S. Cl.
CPC .................. *A61B 17/06004* (2013.01); *A61B 2017/00663* (2013.01); *A61B 2017/0472* (2013.01); *A61B 2017/0496* (2013.01); *A61B 2017/06042* (2013.01)

(58) Field of Classification Search
CPC .. A61B 2017/0496; A61B 2017/00663; A61B 2017/0472; A61B 2017/06042
See application file for complete search history.

(56) References Cited

U.S. PATENT DOCUMENTS

| | | | |
|---|---|---|---|
| 5,836,956 A | 11/1998 | Buelna et al. | |
| 6,136,010 A | 10/2000 | Modesitt et al. | |
| 6,964,668 B2 | 11/2005 | Modesitt et al. | |
| 7,001,400 B1 | 2/2006 | Modesitt et al. | |
| 7,004,952 B2 | 2/2006 | Nobles et al. | |
| 7,235,087 B2 | 6/2007 | Modesitt et al. | |
| 7,625,392 B2 | 12/2009 | Coleman et al. | |
| 7,837,696 B2 | 11/2010 | Modesitt et al. | |
| 7,842,047 B2 | 11/2010 | Modesitt et al. | |
| 7,846,170 B2 | 12/2010 | Modesitt et al. | |
| 7,850,701 B2 | 12/2010 | Modesitt | |
| 8,038,688 B2 | 10/2011 | Modesitt et al. | |
| 8,048,092 B2 | 11/2011 | Modesitt et al. | |
| 8,057,491 B2 | 11/2011 | Modesitt et al. | |
| 8,137,364 B2 | 3/2012 | Zung et al. | |
| 8,172,860 B2 | 5/2012 | Zung et al. | |
| 8,241,305 B2 | 8/2012 | Stone | |
| 8,323,298 B2 | 12/2012 | Modesitt et al. | |
| 8,496,675 B2 | 7/2013 | Chambers | |
| 8,663,248 B2 | 3/2014 | Zung et al. | |
| 9,060,751 B2 | 6/2015 | Martin et al. | |
| 9,149,276 B2 | 10/2015 | Voss | |
| 9,332,981 B2 | 5/2016 | Roorda et al. | |
| 10,271,834 B2 * | 4/2019 | Roorda | A61B 17/06004 |
| 2004/0092964 A1 | 5/2004 | Modesitt et al. | |
| 2006/0069397 A1 * | 3/2006 | Nobles | A61B 17/0469 606/144 |
| 2008/0033459 A1 | 2/2008 | Shafi et al. | |
| 2008/0312686 A1 | 12/2008 | Ellingwood | |
| 2009/0018574 A1 | 1/2009 | Martin | |
| 2010/0179571 A1 | 7/2010 | Voss | |
| 2011/0071567 A1 | 3/2011 | Modesitt et al. | |
| 2012/0035623 A1 | 2/2012 | Bagaoisan et al. | |
| 2012/0245603 A1 * | 9/2012 | Voss | A61B 17/10 606/151 |
| 2014/0180312 A1 | 6/2014 | Zung et al. | |
| 2017/0020511 A1 | 1/2017 | Roorda et al. | |

OTHER PUBLICATIONS

U.S. Appl. No. 13/111,576, filed Sep. 29, 2014, Office Action.
U.S. Appl. No. 13/111,576, filed Aug. 24, 2015, Office Action.
U.S. Appl. No. 13/111,576, filed Feb. 10, 2016, Notice of Allowance.
U.S. Appl. No. 15/149,805, filed Feb. 8, 2018, Office Action.
U.S. Appl. No. 15/149,805, filed Apr. 27, 2018, Office Action.
U.S. Appl. No. 15/149,805, filed Dec. 20, 2018, Notice of Allowance.
U.S. Appl. No. 15/149,805, filed Apr. 10, 2019, Issue Notification.

* cited by examiner

CLOSURE DEVICES AND METHODS

CROSS-REFERENCE TO RELATED APPLICATIONS

This is a continuation application of U.S. patent application Ser. No. 15/149,805, entitled "Closure Devices and Methods," filed May 9, 2016, which is a continuation of Ser. No. 13/111,576, entitled "Closure Devices and Methods", filed May 19, 2011, now U.S. Pat. No. 9,332,981, the disclosures of which are incorporated herein by this reference.

BACKGROUND

1. Technical Field

The present disclosure relates generally to techniques and devices for closing an opening in a body lumen. More particularly, the present disclosure relates to systems, devices, and methods for percutaneous closure of arterial and venous puncture sites, which are usually accessed through a tissue tract.

2. The Relevant Technology

A number of diagnostic and interventional vascular procedures are now performed translumenally. A catheter is introduced to the vascular system at a convenient access location and guided through the vascular system to a target location using established techniques. Such procedures require vascular access, which is usually established using the well-known Seldinger technique. Vascular access is generally provided through an introducer sheath, which is positioned to extend from outside the patient's body into the vascular lumen. When vascular access is no longer required, the introducer sheath is removed and bleeding at the puncture site stopped.

One common approach for providing hemostasis (the cessation of bleeding) is to apply external force near and upstream from the puncture site, typically by manual compression. This approach suffers from a number of disadvantages. For example, the manual compression procedure is time consuming, frequently requiring one-half hour or more of compression before hemostasis is achieved. Additionally, such compression techniques rely on clot formation, which can be delayed until anticoagulants used in vascular therapy procedures (such as for heart attacks, stent deployment, non-optical PTCA results, and the like) wear off. The anticoagulants may take two to four hours to wear off, thereby increasing the time required before completion of the manual compression procedure.

Further, the manual compression procedure is uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation to assure continued hemostasis. During this time, renewed bleeding may occur, resulting in blood loss through the tract, hematoma and/or pseudo-aneurysm formation, as well as arteriovenous fistula formation. These complications may require blood transfusions and/or surgical intervention.

The incidence of complications from the manual compression procedure increases when the size of the introducer sheath grows larger, and/or when the patient is anticoagulated. The compression technique for arterial closure can be risky and is expensive and onerous to the patient. Although using highly trained individuals can reduce the risk of complications, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, the use of bioabsorbable sealing bodies is one example approach that has been proposed. Generally, this example approach relies on the placement of a thrombogenic and bioabsorbable material, such as collagen, at the superficial arterial wall over the puncture site. While potentially effective, this approach suffers from a number of drawbacks. For example, bioabsorbable sealing bodies may lack a solid mechanical attachment of the sealing body to the tissue. Due to the lack of a solid mechanical attachment, the sealing body can wander within the tissue tract or move out of the puncture site, thus causing late bleeds. Conversely, if the sealing body wanders and intrudes too far into the arterial lumen, due to the lack of a solid mechanical attachment, intravascular clots and/or collagen pieces with thrombus attached can form and embolize downstream, causing vascular occlusion.

In addition to not having a solid mechanical attachment to the tissue, the sealing bodies may rely upon expandable materials to achieve hemostasis. Again, the expandable materials lack the security of a hard, mechanical closure, thus potentially causing late bleeds and prolonging hemostasis.

For these reasons, it would be desirable to provide improved devices and methods to seal body lumen puncture sites. It would be particularly desirable to provide percutaneous devices and methods for suturing the puncture sites required for percutaneous vascular procedures.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Embodiments of the present invention provide systems, methods, and devices for closing an opening in tissue. Embodiments of the invention can be configured to close an opening within a body lumen.

For instance, in one exemplary embodiment, a device for closing an opening in tissue includes a body member that has a proximal portion and a distal portion. The proximal portion includes a plurality of proximal slits disposed therein and the distal portion includes a plurality of distal slits disposed therein. The proximal and distal slits cooperate with the body member to facilitate the proximal portion and distal portion changing from delivery configurations to deployed configurations. The proximal portion and the distal portion each change from the delivery configuration to the deployed configuration by axially compressing and radially expanding. The device can also include one or more actuators for moving the proximal and distal portions between the delivery and deployed configurations. The device also includes a plurality of needle guide apertures formed in the proximal portion that are adapted to have at least one needle pass therethrough. At least one cuff is also removably mounted in the distal portion.

According to another implementation of the present invention, a device for closing an opening in a body lumen includes an elongate member, at least one needle, and a closure element. The elongate member has a proximal end, a distal end, a central passage, and at least one needle lumen extending from the proximal end toward the distal end. The at least one needle is disposed within and advanceable from the at least one needle lumen. The closure element extends from the distal end of the elongate member and has a proximal portion, a distal portion, and a waist portion. The proximal portion and the distal portion are each configured to move between a delivery configuration and a deployed configuration. The proximal portion includes a plurality of needle guide apertures and the distal portion has at least one cuff removably mounted therein. The plurality of needle guide apertures guide the at least one needle to the at least one cuff when the proximal and distal portions are in the deployed configurations and as the at least one needle is advanced from the at least one needle lumen.

In still another exemplary embodiment, a closure device that is used in closing an opening in a wall of a body lumen includes an elongate member that has at least one pair of needle lumens extending therethrough. At least one pair of needles are disposed in the at least one pair of needle lumens. The at least one pair of needles are selectively advanceable from the at least one pair of needle lumens. A closure element extends from the elongate member and has a longitudinal axis. The closure element includes a foot portion that has a delivery configuration and a deployed configuration. The foot portion is designed to pass through the opening in the wall of the body lumen when the foot portion is in the delivery configuration. The foot portion also resists passage through the opening in the wall of the body lumen when the foot portion is in the deployed configuration. The foot portion has at least one pair of cuffs removably mounted thereon with a length of suture being connected between the at least one pair of cuffs. The closure element also includes a needle guide portion that has a delivery configuration and a deployed configuration. The needle guide portion has at least one pair of proximal needle guide apertures and at least one pair of distal needle guide apertures. The proximal and distal needle guide apertures guide the at least one pair of needles toward the at least one pair of cuffs when the needle guide portion is in the deployed configuration and as the at least one pair of needles are advanced from the at least one pair of needle lumens.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

As used herein, the term "distal" is generally defined as in the direction of the patient or away from a user of a device. In the context of a medical device intervention with or through a vessel wall, "distal" herein refers to the interior or the lumen side of the vessel wall. Conversely, "proximal" generally means away from the patient or toward the user. In the context of a medical device intervention with or through a vessel wall, "proximal" herein refers to the exterior or outer side of the vessel wall.

The term "suturing" is herein intended to include the process of joining two surfaces or edges together with a fastener or so as to close an aperture, opening, or wound, or join tissues. The fastener is usually a suture such as a thread of material (either polymeric or natural), gut, wire, or the like. The term fastener as used herein also includes clamps, studs, hasps, catches, hooks, rivets, staples, snaps, stitches, VELCROC, buttons, and other coupling members.

Referring to FIGS. 1-5, a suture applying device which is suitable for suturing and sealing of percutaneous vascular puncture sites, such as those made to the femoral artery in a patient's groin, will be described. It will be appreciated, however, that the device of the present invention can be readily adapted for use with punctures made to other hollow body organs and lumens, although it may be necessary to modify the dimensions and other particular aspects of the device to accommodate the different usage environments.

Figure 1:
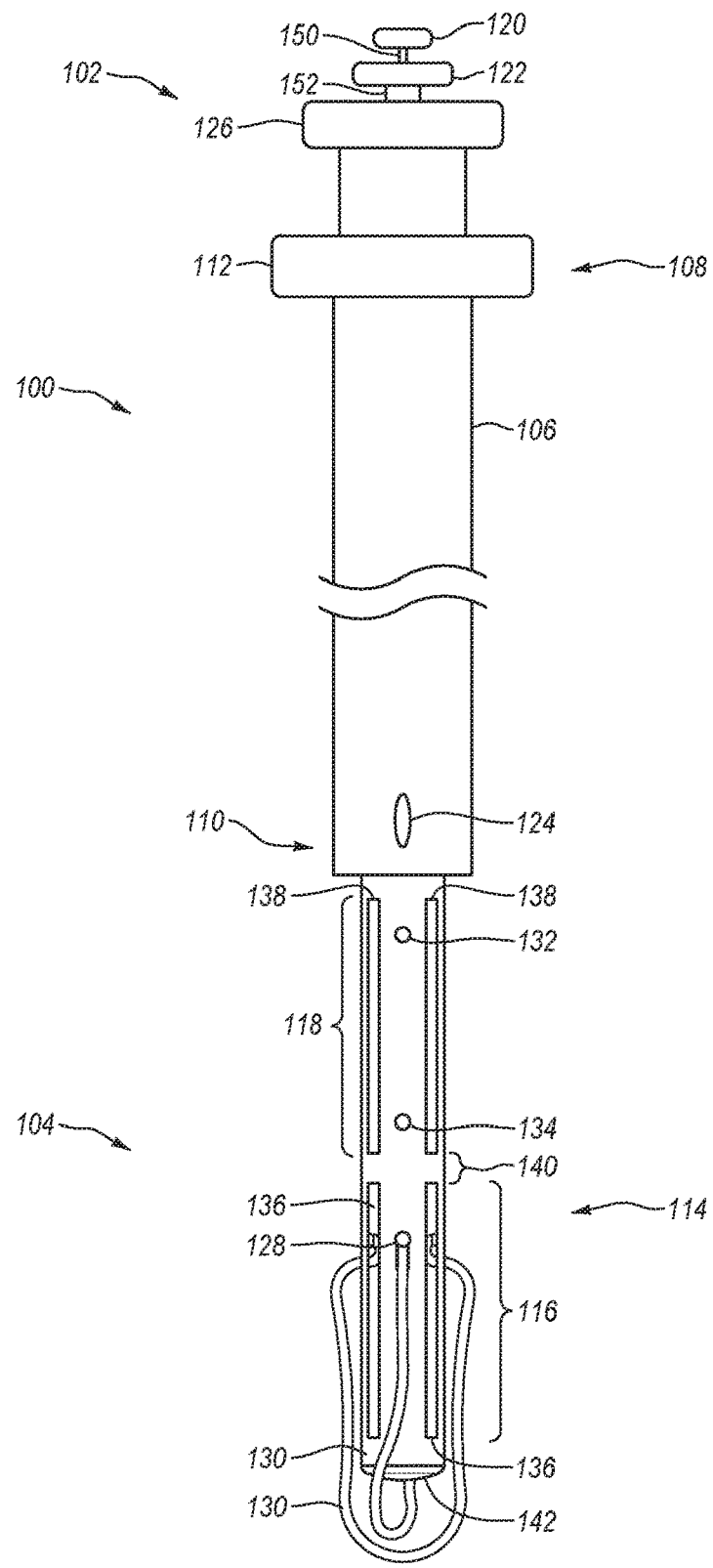
FIG. 1 is an elevation view of a closure device in accordance with one embodiment of the present invention.

FIG. 1 illustrates one example embodiment of a closure device 100. Closure device 100 includes a proximal end 102 and a distal end 104. As shown in FIG. 1, closure device 100 includes an elongate member 106 that has a proximal end 108 and a distal end 110. As discussed in greater detail below, elongate member 106 also includes one or more lumens that extend generally from proximal end 108 to distal end 110. The one or more lumens may be used to facilitate the delivery of device 100 over a guidewire or to delivery one or more needles into a patient. Elongate member 106 is generally tubular and includes a handle 112 at proximal end 108 to facilitate manipulation of device 100 or elongate member 106. In one embodiment elongate member 106 is formed of a rigid material such as a stainless steel or other biocompatible material that is rigid. Alternatively, elongate member 106 may be formed of a flexible material such as those materials utilized to form catheter shafts, introducer sheaths, or other medical devices. Suitable materials include polyvinyl chloride (PVC), peak, PTFE, nylon, or any other similar materials.

Extending beyond distal end 110 of elongate member 106 is a closure element 114. Closure element 114 is also a hollow, generally tubular shaped member and includes a foot portion 116, a needle guide portion 118, and a tip 142. As shown in FIG. 1, foot portion 116 and needle guide portion 118 are each in a delivery configuration that allows closure element 114 to be inserted into a patient. Once inserted, foot portion 116 and needle guide portion 118 can be selectively expanded and subsequently collapsed as discussed below. Handles 120, 122 at proximal end 102 of closure device 100 are operably connected to foot portion 116 and needle guide portion 118, respectively, such that handles 120, 122 can be used to selectively expand and collapse foot portion 116 and needle guide portion 118.

As alluded to above, closure device 100 also includes one or more needles that can be deployed from one or more lumens (such as needle lumen 124) in elongate body 106 into a patient. The one or more needles can be advanced through the needle lumens and into the patient using handle 126. More specifically, handle 126 may be linked to or operably associated with the one or more needles such that the one or more needles advance out of the needle lumens and into the patient as handle 126 is moved distally (i.e., towards distal end 104). Likewise, handle 126 may be adapted to withdraw the one or more needles out of the patient and back into the needle lumens when handle 126 is moved proximally (i.e., away from distal end 104).

Foot portion 116 includes one or more cuffs 128 removably mounted therein. A length of suture 130 is connected to each cuff 128. In the illustrated embodiment, a length of suture is connected between each pair of cuffs 128. When foot portion 116 is deployed in a vessel and the needles are deployed from elongate member 106 into the patient, each needle engages and connects to a cuff 128. Needle guide portion 118 includes proximal and distal needle guide apertures 132, 134 that are arranged on needle guide portion 118 so as to receive the needles therethrough when the needles are deployed from elongate member 106. Needle guide apertures 132, 134 are adapted to guide the needles toward cuffs 128. When the needles are subsequently withdrawn out of the patient, the needles withdraw cuffs 128 out of the patient as well. Drawing cuffs 128 out of the patient pulls sutures 130 through the vessel wall so that sutures 130 may be tied to close a puncture in the vessel wall.

Foot portion 116 and needle guide portions 118 include slits 136, 138, respectively, that enable or facilitate the expansion and contraction of foot portion 116 and needle guide portion 118. The geometric configuration of slits 136, 138, as shown in FIG. 1, may be a generally rectangular configuration. However, in other example embodiments the geometric configuration of slits 136 and/or slits 138 may take various other geometric configurations such as more square, triangular, oval or any other configuration or combination of configurations. Slits 136, 138 may be formed within the wall of closure element 114 using known manufacturing techniques such as cutting, laser cutting, water jet cutting. Alternatively, slits 136, 138 may be integrally formed within closure element 114 during manufacturing such as through the use of injection molding.

Furthermore, and as illustrated in the example embodiment of FIG. 1, slits 136 may have substantially the same configuration and dimensions as slits 138. In other example embodiments, however, slits 136 and slits 138 may have different geometric configuration and/or dimension compared to one another. For example, in one embodiment, slits 136 may have a different length and width as slits 138, or slits 136 may have a different geometric configuration relative to slits 138.

In addition to variations between slits 136 and slits 138, the geometric configuration and the dimensions of slits 136 and/or slits 138 may vary from one slit to the next. For instance, slits 136 may have a variety of different sized and configured slits that make up the plurality of slits 136. Similarly, slits 138 may be made up of a variety of different sized and configured individual slits.

The distance between slits 136 and slits 138 is another aspect of closure element 114 that may vary from one embodiment to the next. In one example embodiment, the distance between slits 136 and slits 138 is a distance that would be approximately equal to the width of a body lumen wall. For example, the distance between slits 136, 138 may be equal to the width of the proximal lumen wall 156, illustrated in FIGS. 6-11. The area of closure element 114 between slits 136, 138 may be referred to as a waist 140. Thus, waist 140 may have a length that is about equal to the width of a lumen wall.

Figure 2:
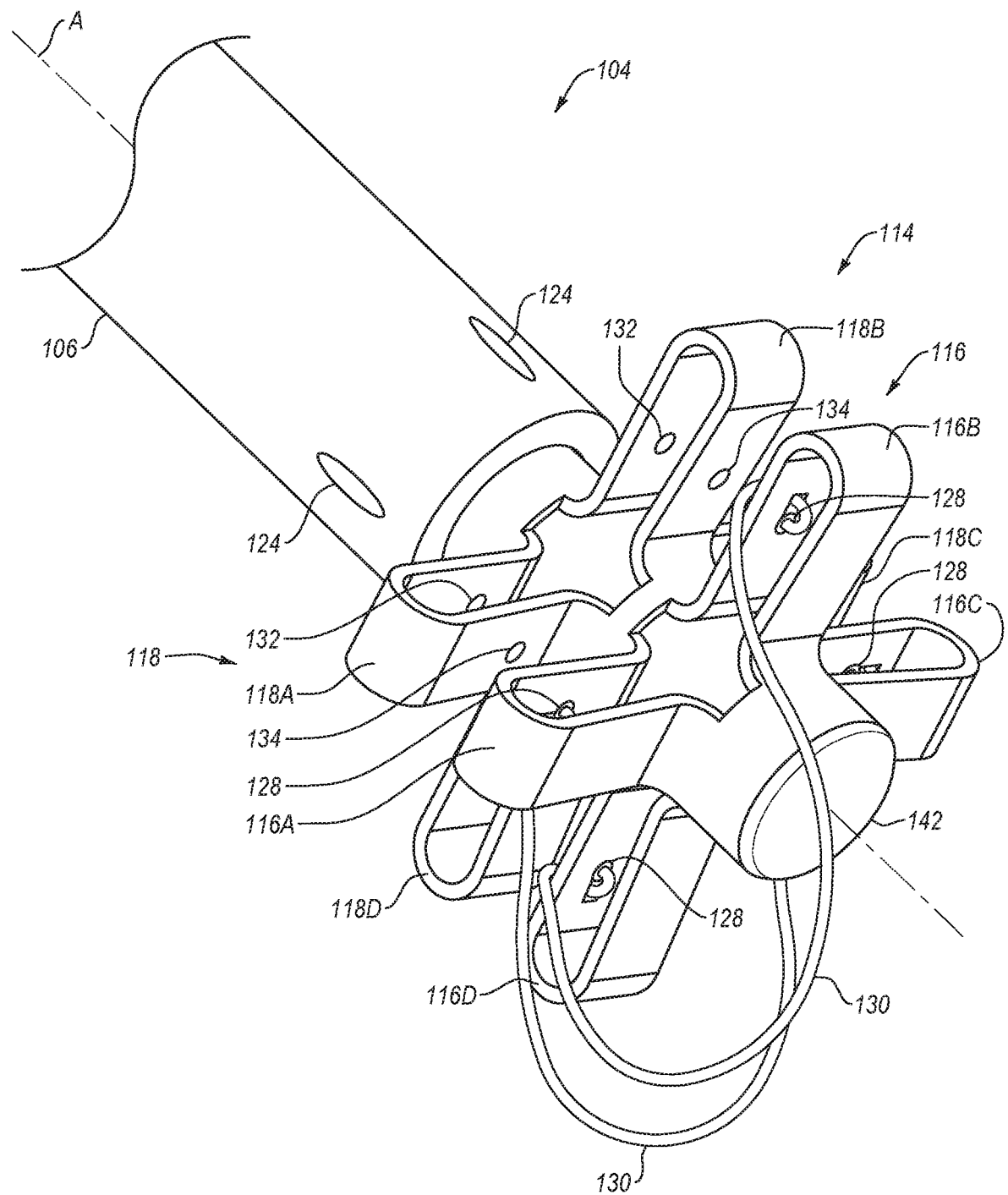
FIG. 2 is a close-up view of the distal end of the closure device of FIG. 1 in a deployed configuration.

Attention is now directed to FIG. 2, which illustrates a perspective view of distal end 104 of closure device 100 with foot portion 116 and needle guide portion 118 deployed to their expanded configurations. In the illustrated embodiment, foot portion 116 and needle guide portion 118 expand generally radially out in four directions to form generally cross shapes. More specifically, foot portion 116 includes four segments or legs 116A, 116B, 116C, 116D that extend away from longitudinal axis A of device 100 in four different directions. Likewise, needle guide portion 118 includes four segments or legs 118A, 118B, 118C, 118D that extend away from axis A in four different directions. Slits 136, 138 in respective foot portion 116 and needle guide portion 118 at least partially define legs 116A, 116B, 116C, 116D, 118A, 118B, 118C, 118D. More specifically, the area between two radially adjacent slits 136 defines a leg or segment of foot portion 116, and the area between two radially adjacent slits 138 defines a leg or segment of needle guide portion 118. Slits 136, 138 allow legs 116A, 116B, 116C, 116D, 118A, 118B, 118C, 118D to radially expand as discussed herein.

In the illustrated embodiment, corresponding legs from foot portion 116 and needle guide portion 118 are aligned with one another. For instance, legs 116A and 118A are radially aligned with one another, legs 116B and 118B are radially aligned with one another, and so on. As a result, the distal opening of each needle lumen 124 is generally aligned with a leg or segment from needle guide portion 118 and foot portion 116. The alignment between the distal opening of each needle lumen 124 and the legs or segments of needle guide portion 118 and foot portion 116 also provides for alignment between the distal opening of each needle lumen 124 and a proximal needle guide aperture 132 and a distal needle guide aperture 134 in needle guide portion 118, as well as with a cuff 128 removably mounted in foot portion 116, when foot portion 116 and needle guide portion 118 are in the deployed configuration.

Although the distal opening of each needle lumen 124 is generally aligned with a proximal needle guide aperture 132, a distal needle guide aperture 134, and a cuff 128, this alignment is not necessarily parallel to longitudinal axis A of device 100. Rather, when closure element 114 is expanded as shown in FIG. 2, proximal needle guide apertures 132 are spaced radially further away from axis A than the distal openings of needle lumens 124. Similarly, distal needle guide apertures 134 are spaced radially further away from axis A than proximal needle guide apertures 132. Likewise, cuffs 128 are spaced radially further away from axis A than distal needle guide apertures 134. It will be understood that needle lumens 124, proximal needle guide apertures 132, distal needle guide apertures 134, and cuffs 128 may also be radially displaced or offset from one another about axis A. Accordingly, the needles may extend radially about axis A as the needles are deployed through needle lumens 124, proximal needle guide apertures 132, and distal needle guide apertures 134, and into cuffs 128.

As shown in FIGS. 1 and 2, cuffs 128 are supported by foot portion 116 and sutures 130 extend from cuffs 128 so that cuffs 128 and sutures 130 are readily releasable from closure element 114. As shown in FIG. 1, for instance, sutures 130 extend from cuffs 128 toward the outside of closure element 114 (when foot portion 116 is in the delivery configuration; or toward the top of foot portion 116 when foot portion is in the expanded configuration as shown in FIG. 2) so that sutures 130 are disposed substantially outside closure element 114. As a result, when foot portion 116 is moved to the expanded position shown in FIG. 2, sutures 130 extend out over the top of foot portion 116. As will be appreciated, positioning cuffs 128 and sutures 130 in this manner allows cuffs 128 and sutures 130 to be readily removed from foot portion 116 so that closure element 114 may be removed from a vessel and sutures 130 may be used to close a puncture site in the vessel.

Figure 2A:
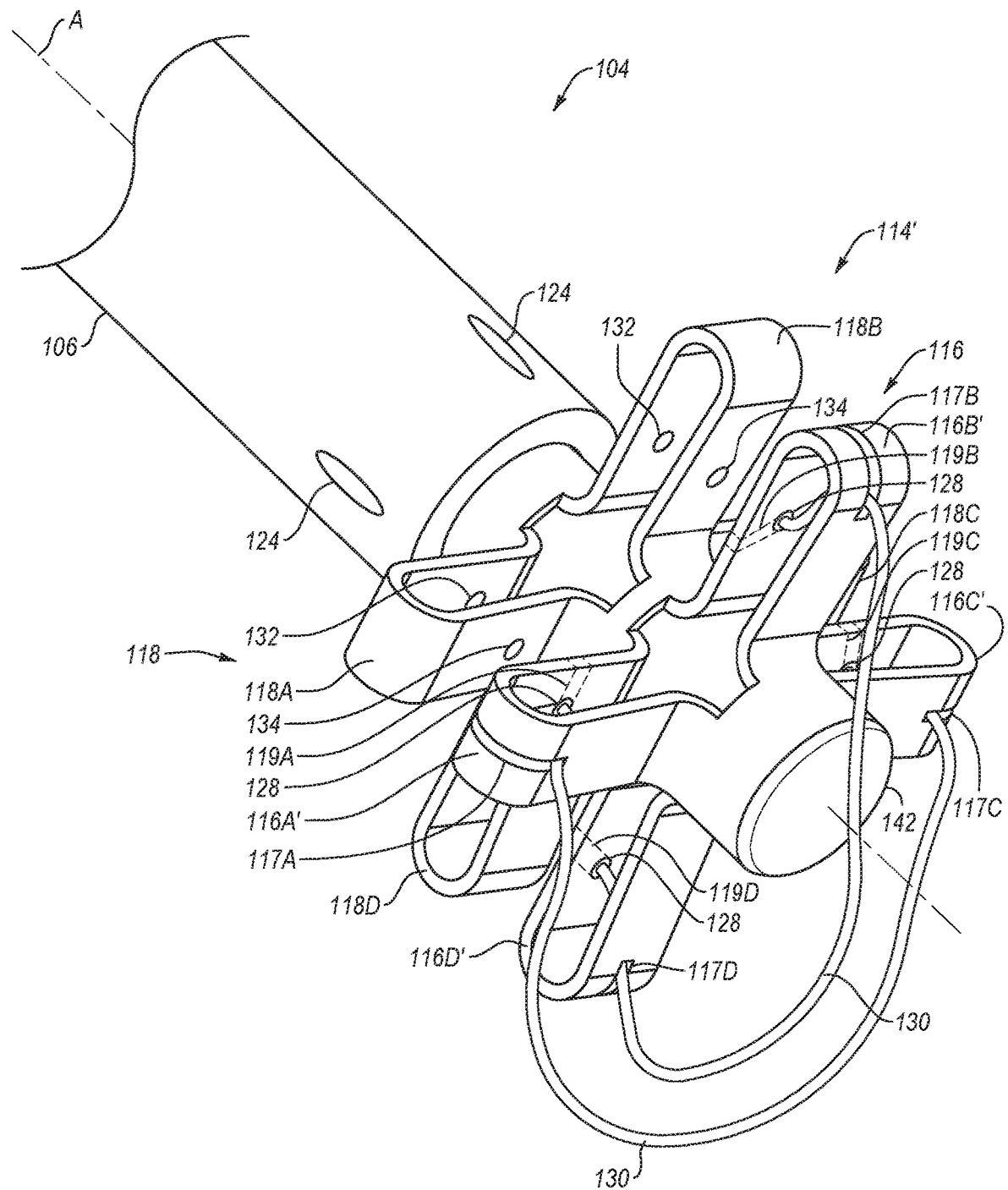
FIG. 2A is a close-up view of the distal end of an alternative embodiment of a closure device, the closure device having suture relief slots formed therein.

Although FIGS. 1 and 2 illustrate sutures 130 extending out of closure element 114, sutures 130 may also extends toward the inside of closure element 114. For instance, FIG. 2A illustrates an alternative embodiment of a closure element 114'. Closure element 114' is similar to identical to closure element 114 in many respects. However, sutures 130' extend from cuffs 128' toward the inside of closure element 114' (when foot portion 116' is in the delivery configuration; or toward the bottom of foot portion 116' when foot portion is in the expanded configuration as shown in FIG. 2A). To allow sutures 130' to be released from or prevent sutures 130' from being caught in foot portion 116' when sutures 130' are passed through a vessel wall or when closure element 114' is removed from a vessel, foot portion 116' may include one or more suture relief slits on each of foot portion leg 116A, 116B, 116C, 116D.

For instance, as shown in FIG. 2A, legs 116A, 116B, 116C, 116D include suture relief slits 117A, 117B, 117C, 117D, respectively. In the illustrated embodiment, suture relief slits 117A, 117B, 117C, 117D extend along a length of legs 116A, 116B, 116C, 116D and are sized to allow sutures 130' to pass therethrough as shown. When cuffs 128' are removed from foot portion 116', sutures 130' are able to slide out of suture relief slits 117A, 117B, 117C, 117D, thereby separating or releasing sutures 130' from foot portion 116'. Sutures 130' may also be separated or released from foot portion 116' when foot portion 116' is moved from the illustrated expanded configuration to a delivery configuration similar to that shown in FIG. 1. As foot portion 116' is moved from the expanded configuration to the delivery configuration, sutures 130' may slide out of suture relief slits 117A, 117B, 117C, 117D, thereby separating or releasing sutures 130' from foot portion 116'.

While suture relief slits 117A, 117B, 117C, 117D have been shown and described as being generally linear slits extending along the length of legs 116A, 116B, 116C, 116D, suture relief slits may be formed in other ways. For instance, FIG. 2A also illustrates in phantom lines suture relief slits 119A, 119B, 119C, 119D that extend from cuffs 128' toward the sides of legs 116A, 116B, 116C, 116D. Like slits 117A, 117B, 117C, 117D, slits 119A, 119B, 119C, 119D may be sized to allow sutures 130' to pass therethrough to separate or release sutures 130' from foot portion 116'. Slits 119A, 119B, 119C, 119D may be oriented perpendicularly to slots 136. Alternatively, slits 119A, 119B, 119C, 119D may be at some other angle relative to slots 136 to allows sutures 130' to more easily pass therethrough when cuffs 128' are removed from foot portion 116' or when foot portion 116' is moved from an expanded configuration to a delivery configuration.

Figure 3:
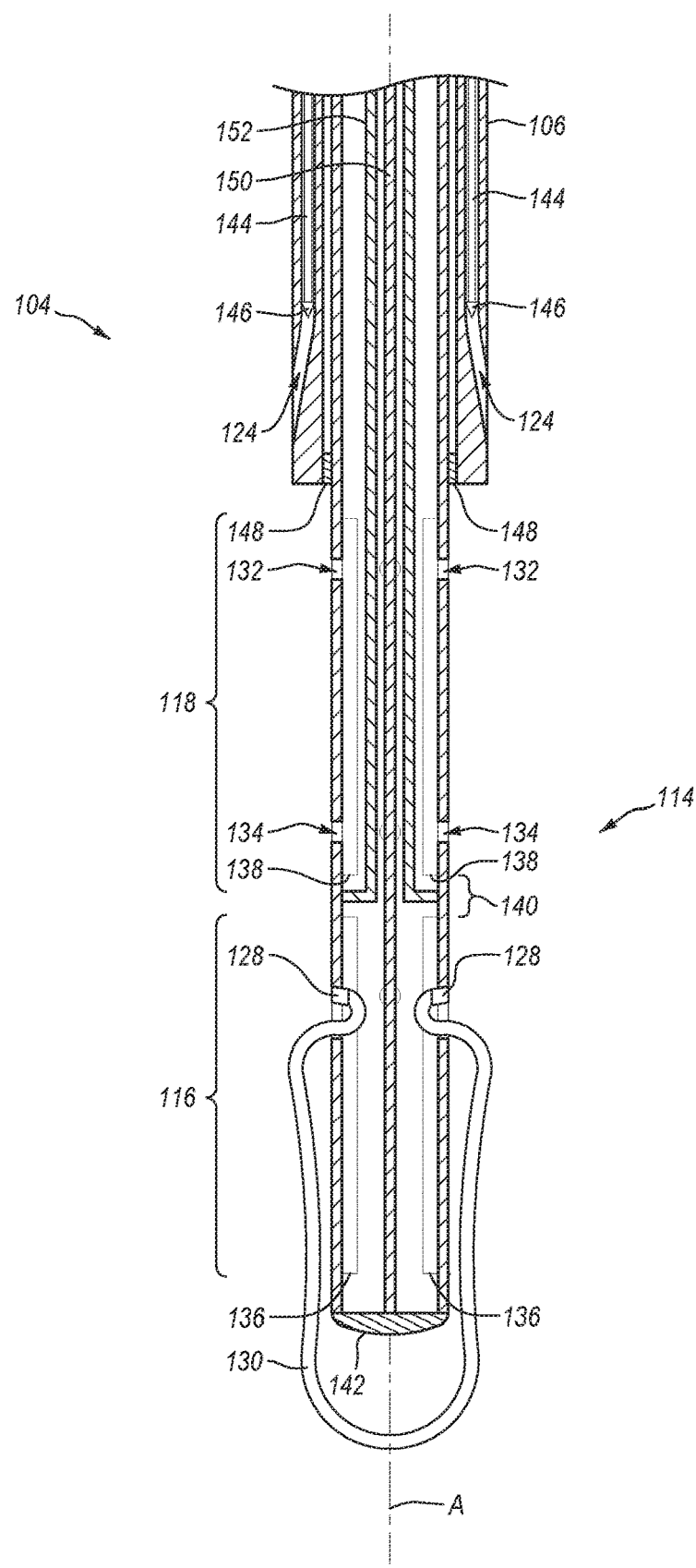
FIG. 3 is a cross-sectional view of the distal end of the closure device of FIG. 1 in a delivery configuration.
Figure 4:
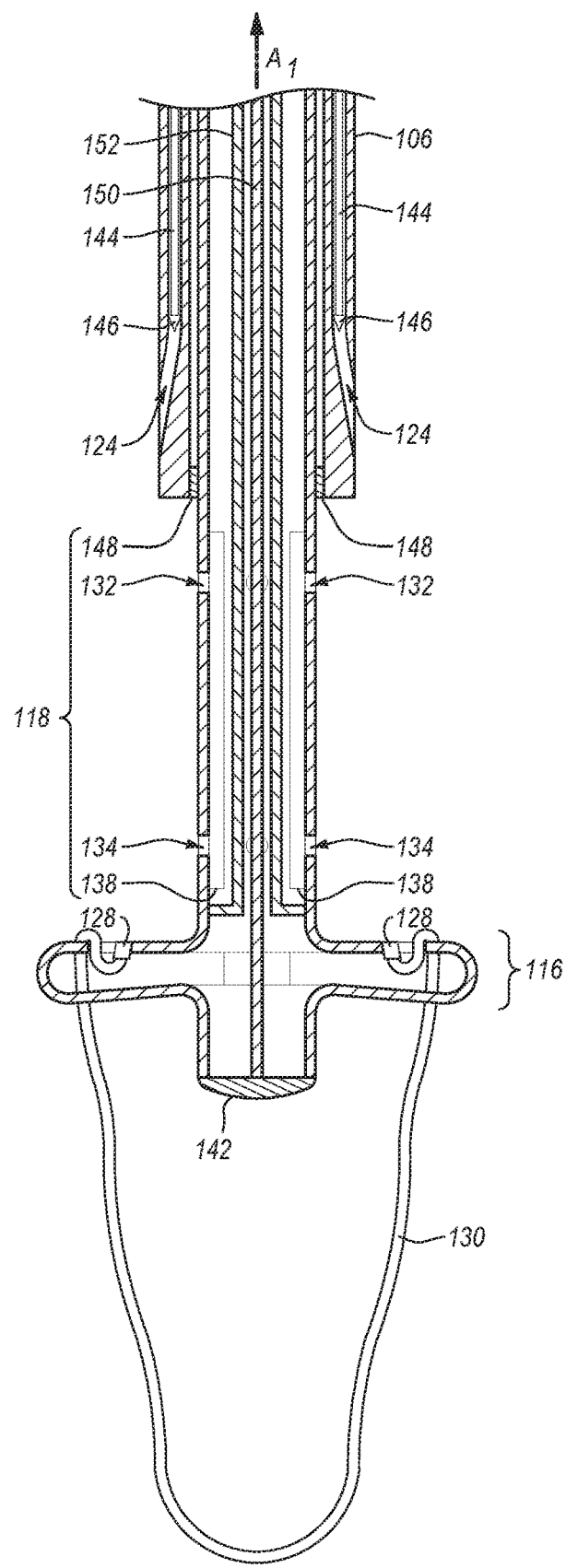
FIG. 4 is a view similar to FIG. 3, except that a foot portion of the distal end has been expanded.
Figure 5:
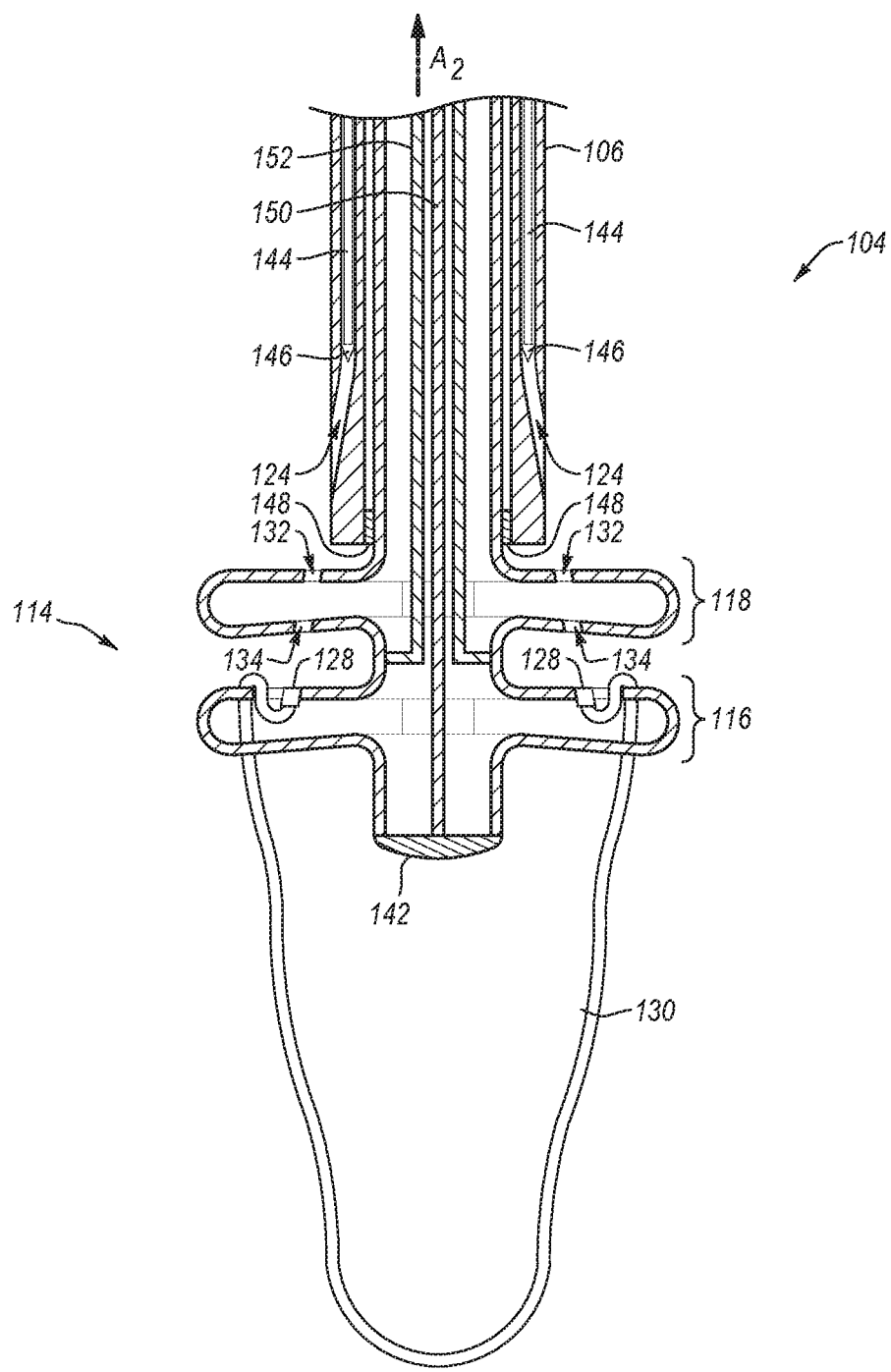
FIG. 5 is a view similar to FIG. 4, except that a needle guide portion of the distal end has been expanded.

Attention is now directed to FIGS. 3-5, which illustrate cross-sectional views of distal end 104 of the embodiment shown in FIGS. 1 and 2, and how closure element 114 is deployed from a delivery configuration to an expanded or a deployed configuration. Although FIGS. 3-5 illustrate specific types of mechanisms for moving closure element 114 between the delivery and deployed configuration, it will be understood that these mechanisms are merely exemplary. One of ordinary skill in the art will recognize other mechanisms that may be employed to move closure element 114 between the delivery and deployed configurations.

With specific reference to FIG. 3, a cross-sectional view of distal end 104 is illustrated in the delivery configuration. In other words, distal end 104 may be inserted at least partially into a patient when distal end 104 is in the configuration shown in FIG. 3. As mentioned above, elongate member 106 includes a plurality of needle lumens 124. Each needle lumen 124 is designed to have a needle 144 positioned therein. As shown in FIG. 3, needles 144 may be positioned within needle lumens 124 such that the distal tips 146 thereof are positioned within needle lumens 124. The distal ends of needle lumens 124 open on an outer circumferential surface of elongate member 106. As a result, upon distal movement of handle 126 (FIG. 1), distal tips 146 of needles 144 are deployed out of the distal ends of needle lumens 124 in a direction that is both away from proximal end 102 and radially away from axis A.

According to the presently illustrated embodiment, closure element 114 extends both beyond distal end 110 of elongate member 106 as well as at least partially into elongate member 106. Nevertheless, in other embodiments closure element 114 does not extend into elongate member 106. For instance, closure element 114 may be attached to or integrally formed on distal end 110 of elongate member 106 without extending substantially into elongate member 106.

In some embodiments it is desirable to link closure element 114 and elongate member 106 together such that a portion of closure element 114 and elongate member 106 do not move relative to one another while another portion of closure element 114 is able to move relative to elongate member 106. For instance, as discussed in greater detail below, during deployment it may be desirable to prevent the proximal end of closure element 114 from moving into or relative to elongate member 106 while allowing one or more other portions of closure element 114 to move relative to elongate member 106. Accordingly, a retaining ring 148 is disposed between elongate member 106 and closure element 114. Retaining ring 148 may be a mechanical fastener or member that is attached to both elongate member 106 and closure element 114 so as to prevent relative movement therebetween. Alternatively, retaining ring 148 may create a friction fitting between elongate member 106 and closure element 114. Retaining ring 148 may also be an adhesive that connects elongate member 106 and closure element 114. Still further, retaining ring 114 may be a feature formed on one or both of elongate member 106 and closure element 114 that prevents relative movement. In other embodiments, retaining ring 148 may be omitted when elongate member 106 and closure element 114 are integrally formed.

As shown in FIG. 3, device 100 also includes rods 150, 152. Rod 150 is connected between handle 120 (FIG. 1) and tip 142 (or, alternatively, the distal end of foot portion 116), and rod 152 is connected between handle 122 (FIG. 1) and waist 140 (or, alternatively, the distal end of needle guide portion 118). Rods 150, 152 are adapted to move foot portion 116 and needle guide portion 118 from the delivery configuration to the deployed configuration when handles 120, 122 are moved proximally.

With reference to FIG. 4, the manner in which foot portion 116 is moved to the deployed configuration will be discussed. In order to move foot portion 116 from the delivery configuration shown in FIGS. 1 and 3 to the deployed configuration shown in FIG. 4, rod 152 is held stationary via handle 122 while rod 150 is moved proximally in the direction of arrow $A_1$. The proximal movement of handle 120 causes tip 142 to also move proximally in the direction of arrow $A_1$. By holding rod 152 stationary, waist 140 is held stationary relative to tip 142. As a result of waist 140 staying stationary and tip 142 moving proximally, foot portion 116 is axially compressed when rod 150 is moved proximally and rod 152 is held stationary. Slits 136 and the axial compression of foot portion 116 causes foot portion legs 116A, 116B, 116C, 116D to fold or otherwise radially expand as shown in FIGS. 2 and 4. When foot portion 116 is moved to the deployed configuration, cuffs 128 face generally proximally toward needle lumens 124. Accordingly, when foot portion 124 is in the deployed configuration, cuffs 128 are oriented so that needles 144 may be deployed and engage cuffs 128, as will be discussed in detail below.

Once foot portion 116 has been moved to the deployed configuration, needle guide portion 118 can also be moved to the deployed configuration. As shown in FIG. 5, moving needle guide portion 118 to the deployed configuration can be accomplished by moving rod 152, via handle 122 (FIG. 1), proximally in the direction of arrow $A_2$. Proximal movement of rod 152 causes waist 140 to also move proximally in the direction of arrow $A_2$. The connection made between closure element 114 and elongate member 106 with retaining ring 148 prevents the proximal end of needle guide portion 118 from moving proximally as rod 152 is moved proximally. As a result of the proximal end of needle guide portion 118 staying stationary and waist 140 moving proximally, needle guide portion 118 is axially compressed when rod 152 is moved proximally. Slits 138 and the axial compression of needle guide portion 118 causes needle guide legs 118A, 118B, 118C, 118D to fold or otherwise radially expand as shown in FIGS. 2 and 5. When needle guide portion 118 is moved to the deployed configuration, needle guides apertures 132, 134 are aligned between needle lumens 124 and cuffs 128. Accordingly, when needle guide portion 118 is in the deployed configuration, needle guide apertures 123, 134 are positioned so that needles 144 may be deployed therethrough and guided into cuffs 128, as discussed herein.

As will be appreciated, foot and needle guide portions 116, 118 may be moved back to the delivery configuration shown in FIG. 3 by generally reversing the previously described steps. For instance, needle guide portion 118 may be moved from the deployed configuration shown in FIG. 5 back to the delivery configuration by moving rod 152, via handle 122 (FIG. 1), distally in a direction generally opposite to the direction of arrow $A_2$ and relative to elongate member 106. By moving rod 152 distally and relative to elongate member 106, needle guide portion 118 is axially expanded, thereby causing needle guide legs 118A, 118B, 118C, 118D to unfold or be drawn radially inward toward axis A and back to the delivery configuration shown in FIG. 3.

Likewise, foot portion 116 may be moved from the deployed configuration shown in FIGS. 4 and 5 back to the delivery configuration shown in FIG. 3 by moving rod 150, via handle 120 (FIG. 1), distally in a direction generally opposite to the direction of arrow $A_1$ and relative to rod 152 (and thus waist 140). By moving rod 150 distally and relative to rod 152, foot portion 116 is axially expanded, thereby causing foot legs 116A, 116B, 116C, 116D to unfold or be drawn radially inward toward axis A and back to the delivery configuration shown in FIG. 3.

Figure 6:
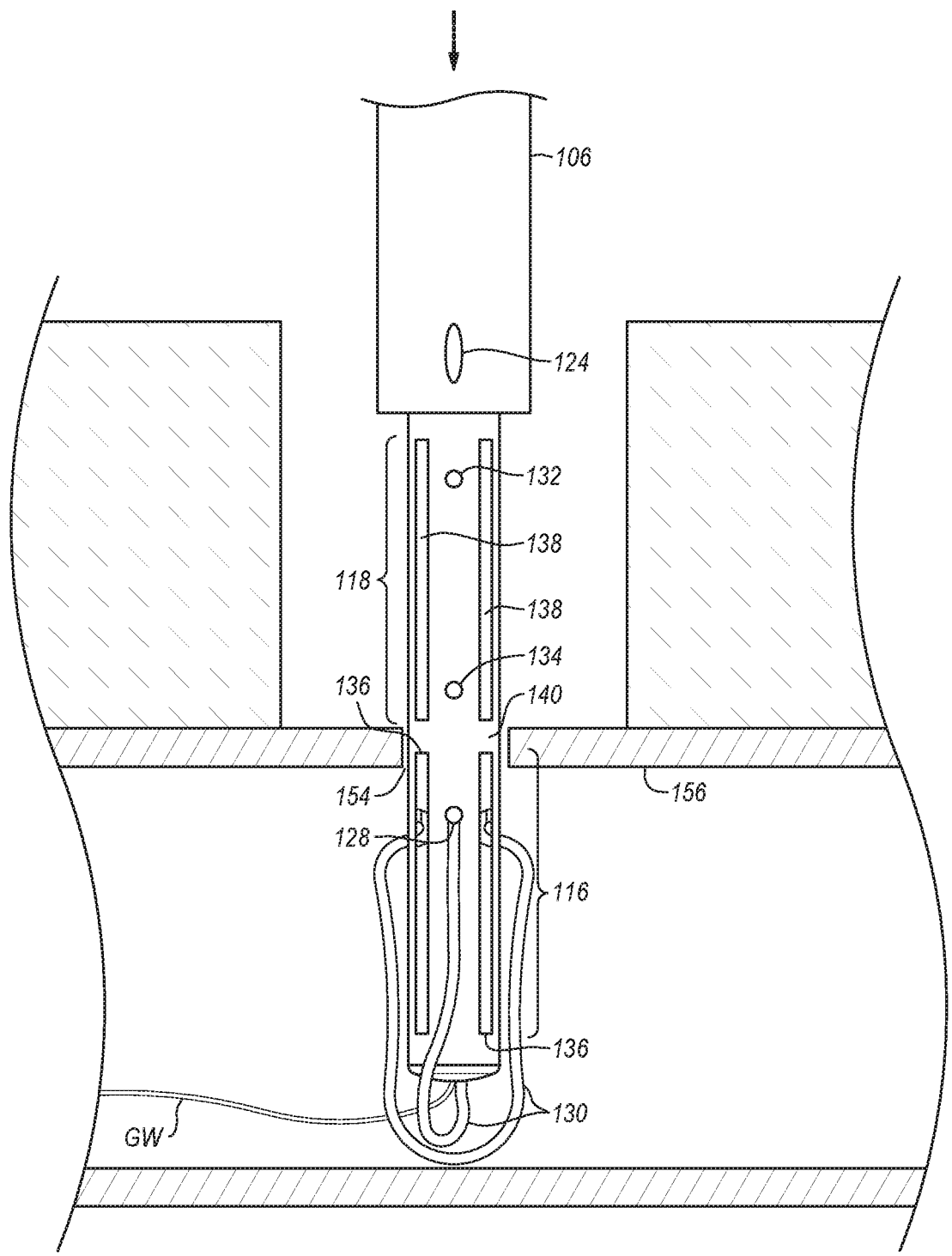
FIG. 6 is a close-up view of the distal end of the closure device of FIG. 1 inserted partially into a vessel through a puncture site.
Figure 7:
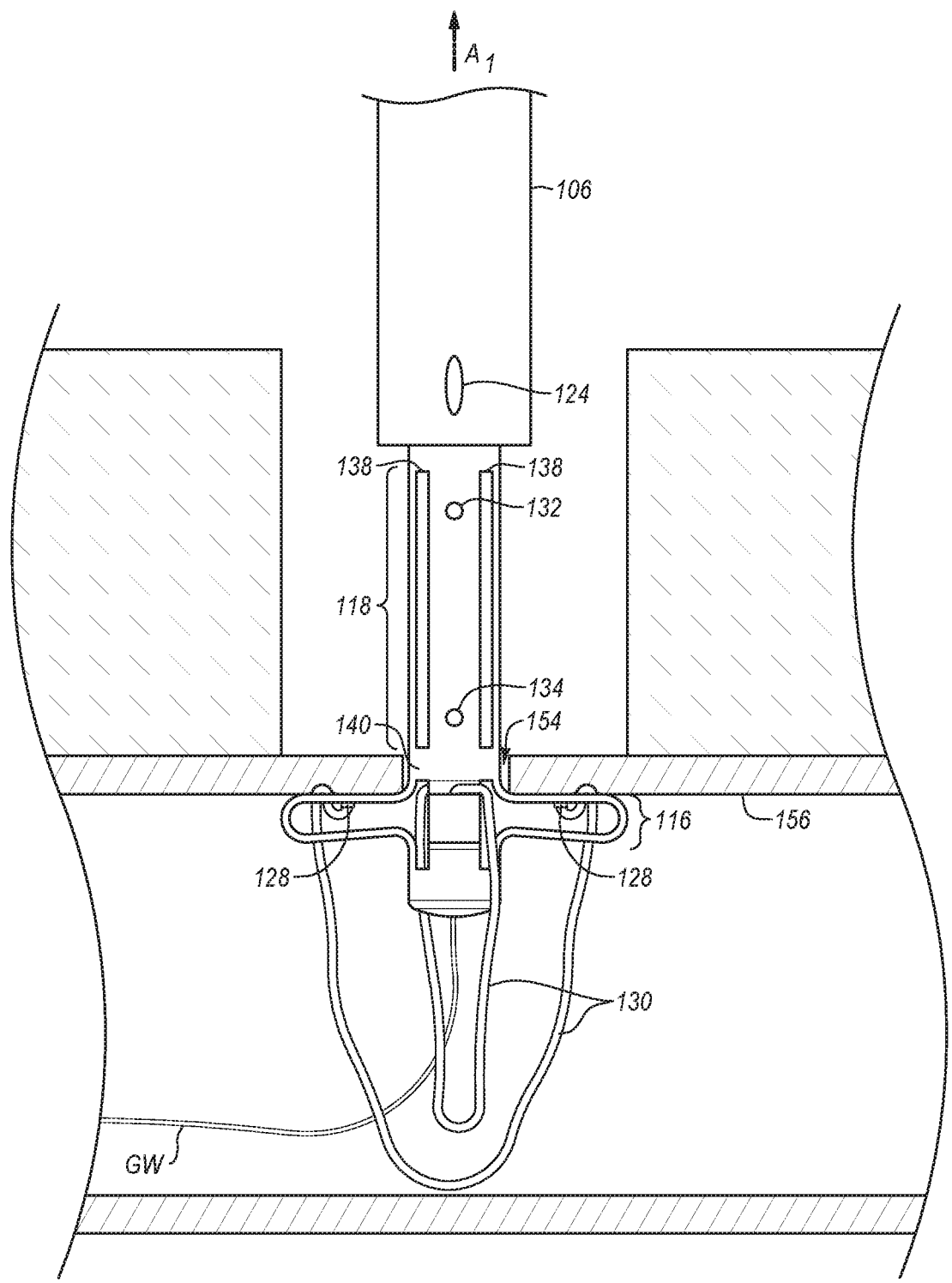
FIG. 7 is a view similar to FIG. 6, except that the foot portion of the distal end has been expanded within the vessel.

With reference to FIGS. 6-12, one exemplary method of using device 100 will be discussed. As shown in FIG. 6, distal end 104 of device 100 is inserted into a patient such that foot portion 116 passes through a puncture 154 in a lumen wall 156. As with many transluminal procedures, device 100 may be introduced into the body lumen using a guidewire GW. Once foot portion 116 is positioned within the body lumen, foot portion 116 is moved to the delivery configuration as shown in FIG. 7. As discussed above, foot portion may be moved to the deployed configuration by holding rod 152 (via handle 122) stationary while moving rod 150 (via handle 120) proximally, thereby axially compressing and radially expanding foot portion 116. Once foot portion 116 is in the deployed configuration, device 100 may be moved proximally so that foot portion legs 116A, 116B, 116C, 116D engage the interior surface of lumen wall 156. In this manner foot legs 116A, 116B, 116C, 116D may be used as locators to ensure proper placement of closure element 114 within the body lumen.

Figure 8:
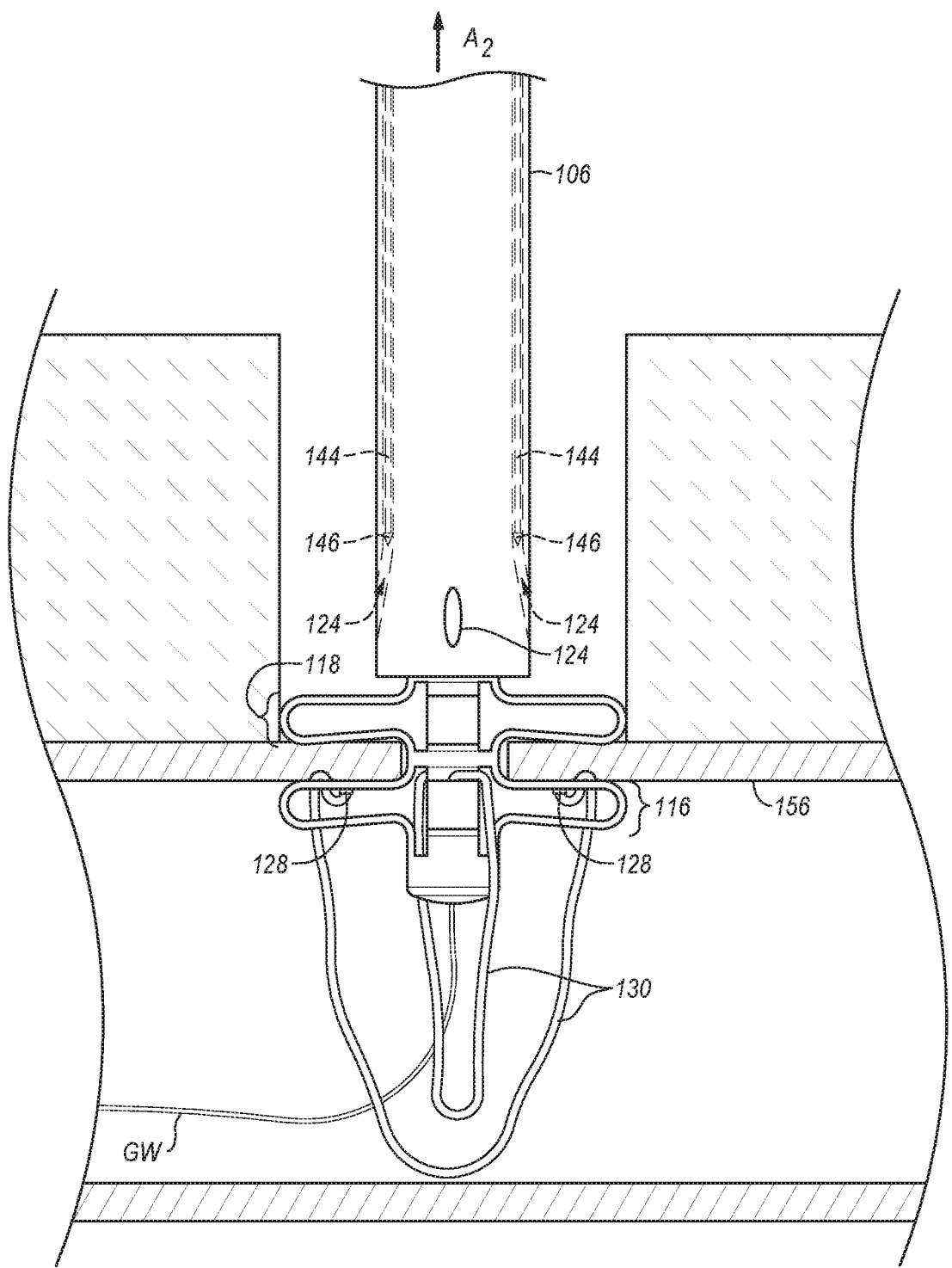
FIG. 8 is a view similar to FIG. 7, except that the needle guide portion of the distal end has been expanded outside the vessel so that the vessel wall is held between the foot portion and the needle guide portion.

Once foot portion 116 has been deployed and positioned within the body lumen as desired, needle guide portion 118 is deployed as shown in FIG. 8. As noted above, needle guide portion 118 is moved to the deployed position by drawing rod 152 (via handle 122) proximally, thereby axially compressing and radially expanding needle guide portion 118. As can be seen in FIG. 8, when foot and needle guide portions 116, 118 are deployed, lumen wall 156 is held therebetween and closure element 114 substantially closes off puncture 154.

Figure 9:
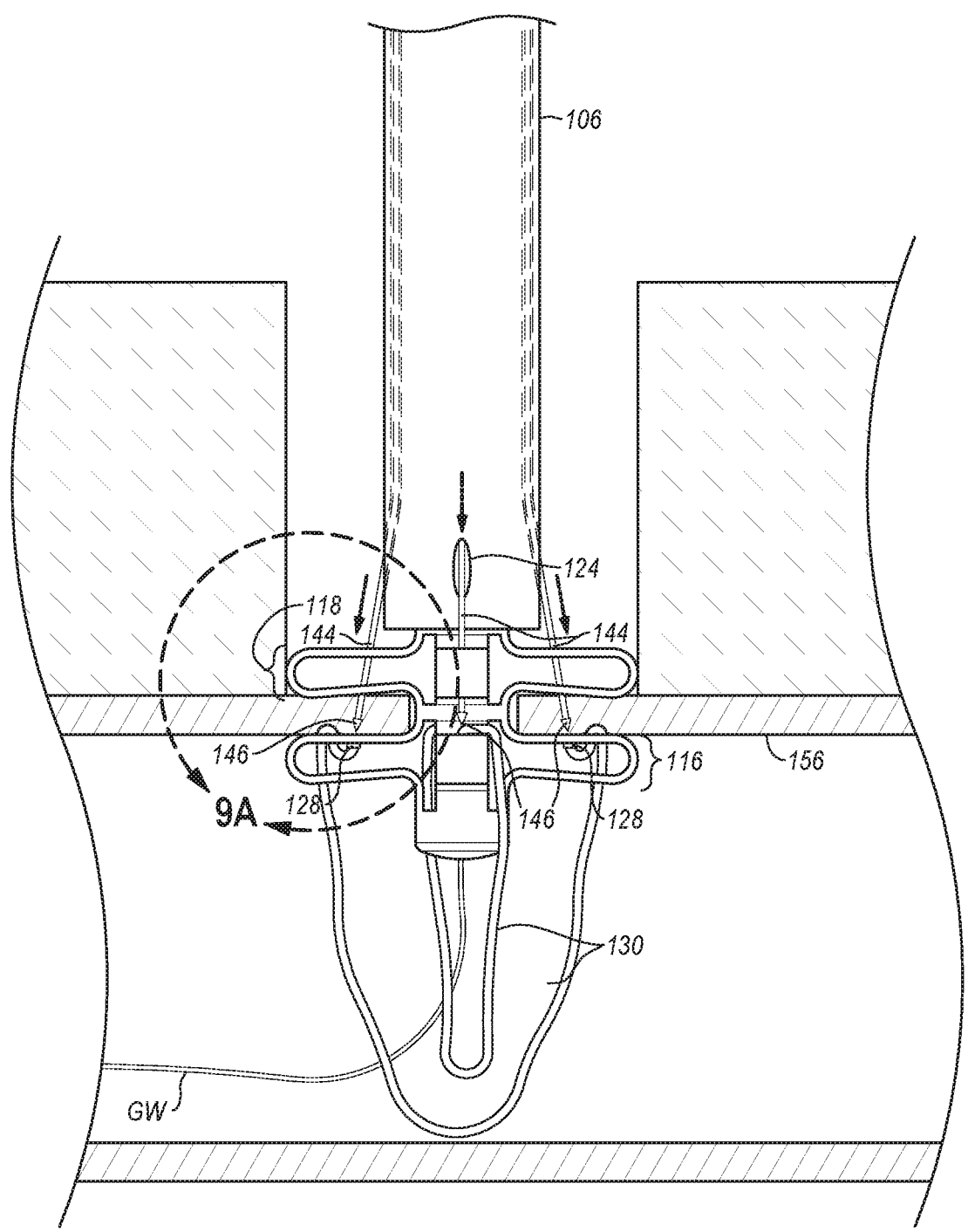
FIG. 9 is a view similar to FIG. 8, except that needles have been deployed through the needle guides, through the vessel wall, and towards cuffs mounted on the foot portion.
Figure 9A:
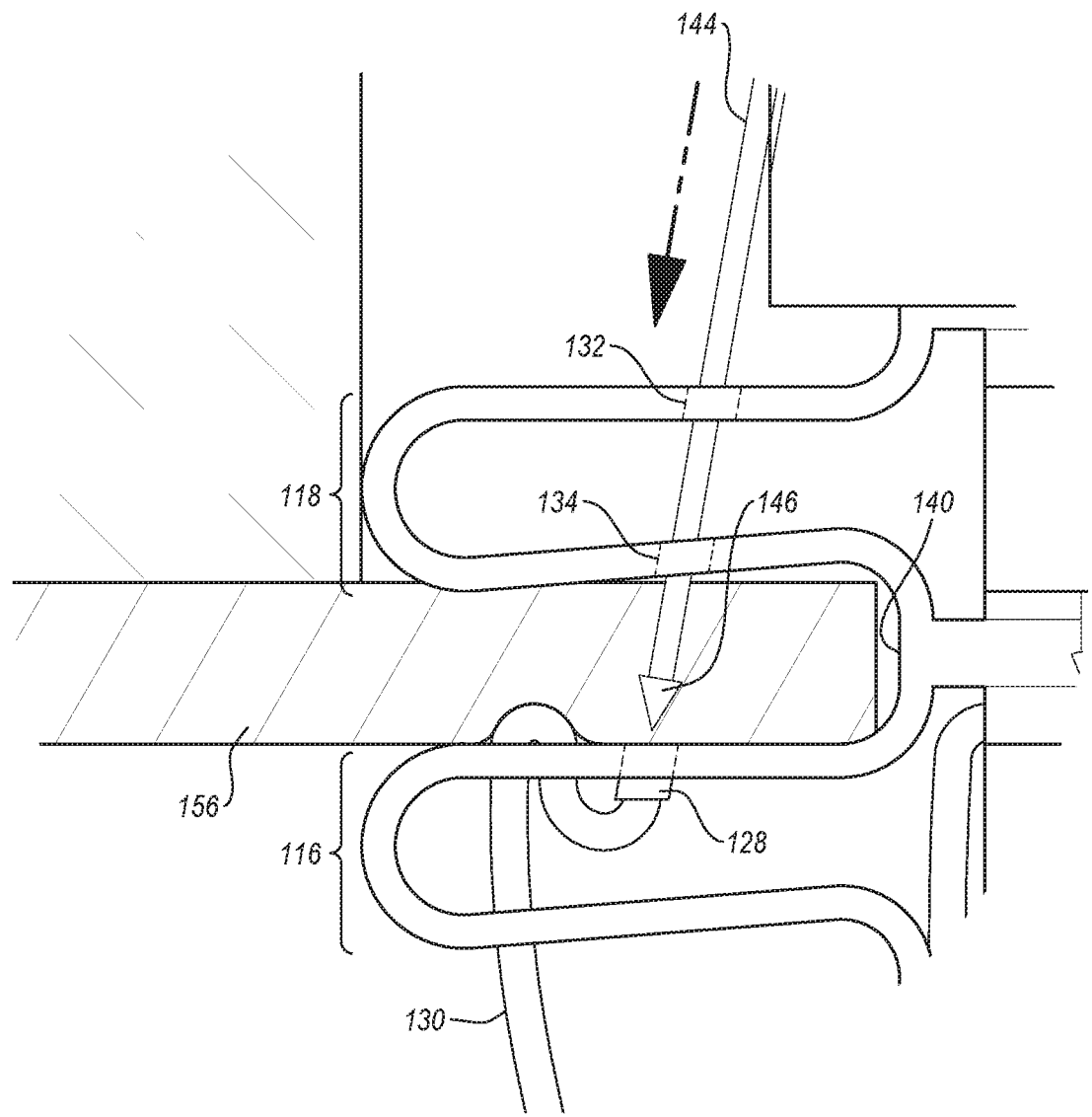
FIG. 9A is a detail view taken from FIG. 9, showing a needle passing through the needle guides, the vessel wall, and toward a cuff in the foot portion.

Once closure element 114 is deployed as shown in FIG. 8, needles 144 are advanced from needle lumens 124 as shown in FIG. 9. As discussed above, needles 144 may be advanced out of needle lumens by moving handle 126 (FIG. 1) distally. The advancement of needles 144 out of needle lumens 124 causes needles 144 to extend distally and at least partially radially away from axis A. More specifically, as shown in FIG. 9A, needles 144 extend out of needle lumens 124 at an angle relative to axis A so that needles 144 will pass through lumen wall 156. Needle guide apertures 132, 134 are aligned with needle lumens 124 and cuffs 128 so that needles 144 will pass through needle guide apertures 132, 134 and to cuffs 128 upon advancement of needles 144 out of needle lumens 124.

As discussed above, proximal needle guide apertures 132, distal needle guide apertures 134, and cuffs 128 are progressively spaced radially further away from axis A and are aligned with needle lumens 124. The arrangement of proximal needle guide apertures 132 and distal needle guide apertures 134 is designed to guide needles 144 to cuffs 128 as shown in FIG. 9A. Thus, as needles 144 extend distally and radially further away from axis A, needles 144 will pass through proximal needle guide aperture 132, then through distal needle guide aperture 134, and then into cuff 128.

Once needle 144 is inserted into cuff 128, needle tip 146 securely engages cuff 128 to connect cuff 128 to needle 144. Needle tip 146 may securely engage cuff 128 in any suitable manner. For instance, as shown in FIG. 9A, needle tip 146 may be generally conical in shape with a proximal surface, and cuff 128 may have a receptacle with one or more features, such as tabs, protrusions, or the like, that engage the proximal surface of needle tip 146. When needle tip 146 is received within cuff 128, the one or more features engage the proximal surface of needle tip 146 and prevent needle tip 146 from being removed from cuff 128.

Figure 10:
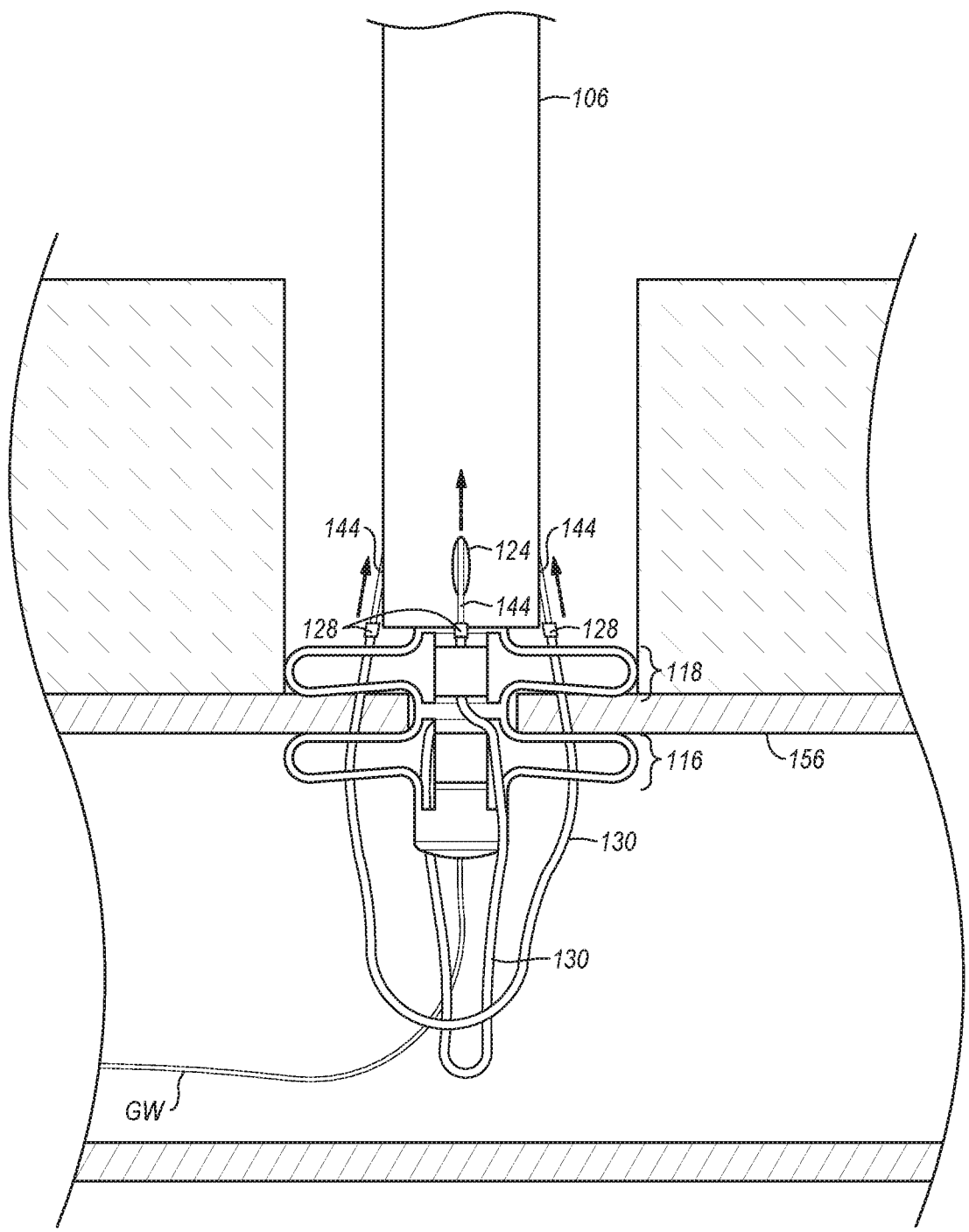
FIG. 10 is a view similar to FIG. 9, except that the needles have been drawn proximally after engaging the cuffs, thereby drawing the cuffs and attached sutures through the vessel wall.

With needle tips 146 securely connected to cuffs 128, needles 144 may be withdrawn out of the patient by moving handle 126 proximally. As needles 144 are withdrawn, cuffs 128 are also withdrawn out of the patient. More specifically, since cuffs 128 are securely connected to needles 144, withdrawal of needles 144 also causes cuffs 128 to be withdrawn. Even more specifically, as shown in FIG. 10, as needles 144 are drawn back through lumen wall 156, through distal needle guide aperture 134, and through proximal needle guide aperture 132, cuffs 128 are likewise drawn therethrough. As can also be seen in FIG. 10, since suture 130 is connected between cuffs 128, the ends of suture 130 are also drawn through lumen wall 156. As a result, the opposing ends of each suture 130 extend through opposing sides of lumen wall 156 so that each suture 130 spans puncture 154.

Figure 11:
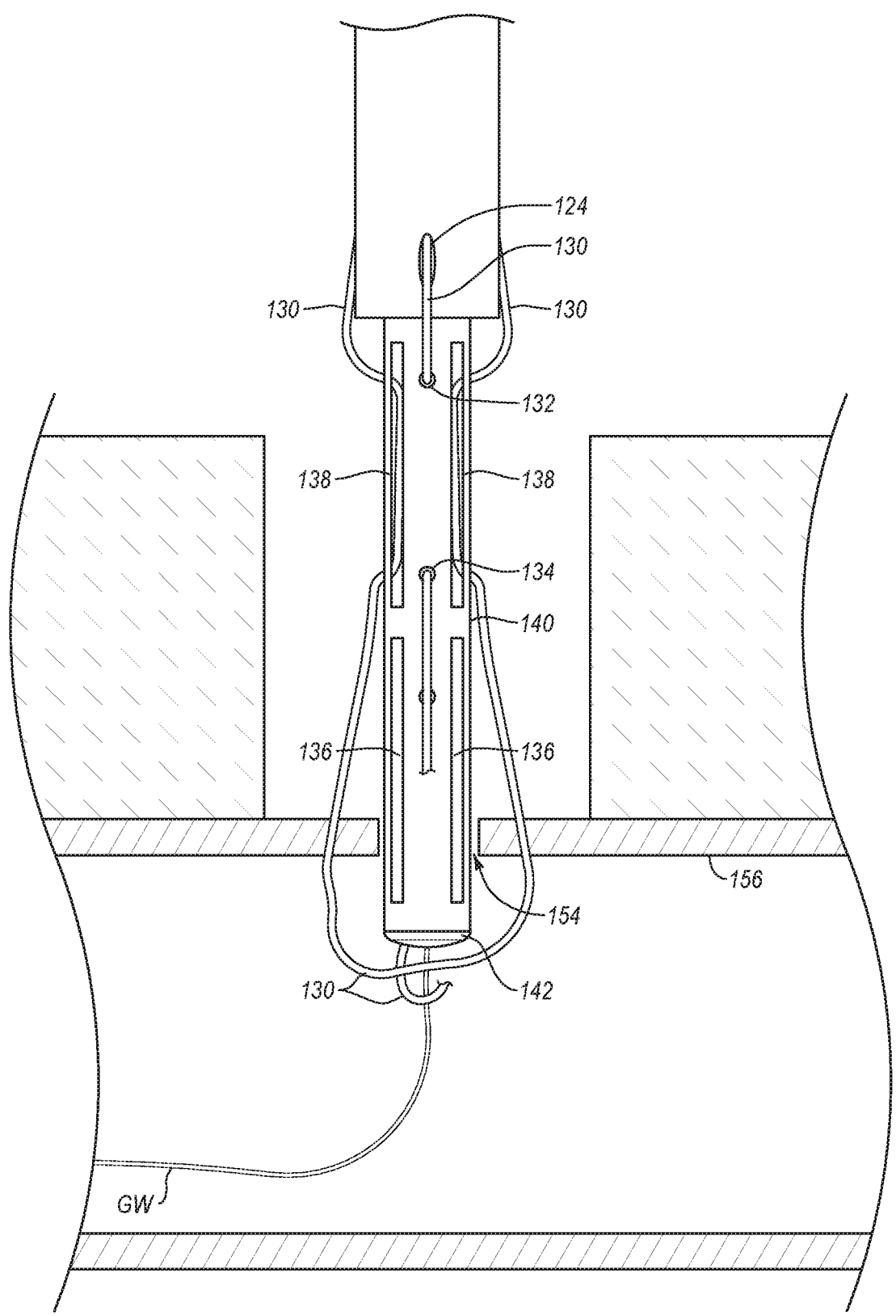
FIG. 11 illustrates the needles completely withdrawn into the elongate member and the foot and needle guide portions collapsed prior to removal of the distal end from the vessel.

Needles 144 may be withdrawn completely back into needle lumens 124 along with cuffs 128 as shown in FIG. 11. Needle guide portion 118 and foot portion 116 are then moved back to the delivery configuration as also shown in FIG. 11. As discussed above, needle guide portion 118 is moved from the deployed configuration to the delivery configuration by moving rod 152, via handle 122, distally to axially expand and radially contract needle guide portion 118. Similarly, foot portion 116 is moved from the deployed configuration to the delivery configuration by moving rod 150, via handle 120, distally to axially expand and radially contract foot portion 116.

Figure 12:
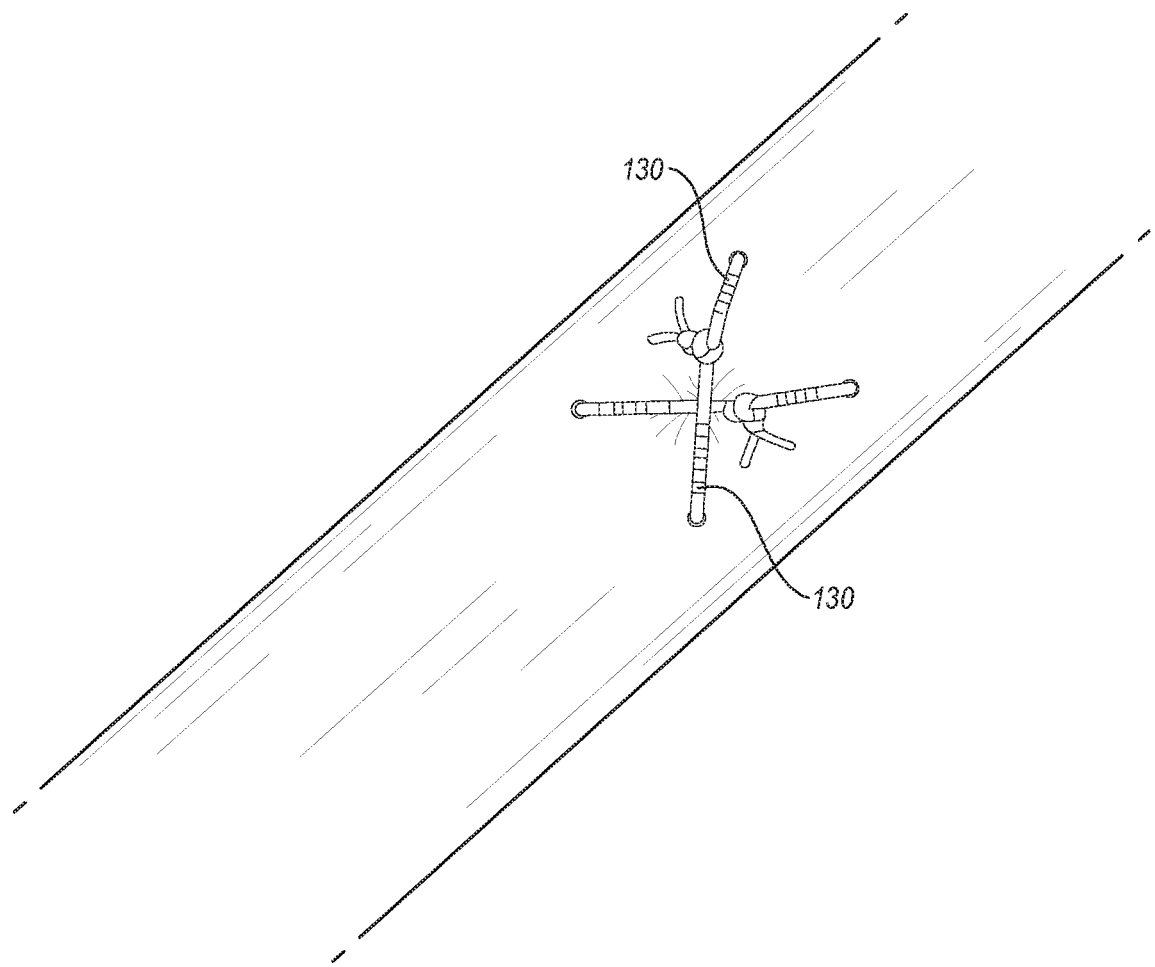
FIG. 12 illustrates the sutures tied to close the opening in the vessel wall.

Once needle guide portion 118 and foot portion 116 are in the delivery configuration, closure element 114 can be removed from the patient, leaving sutures 130 spanning puncture 154 and extending out of lumen wall 156. Sutures 130 can be secured to close puncture 154 as shown in FIG. 12. Sutures 130 can be secured in any suitable manner, including by tying or with clamps, clips, or other closure devices.

Although closure device 100 has been described herein in particular detail, it will be appreciated that a closure device according to the present invention may take other forms or include various modifications to the devices described herein. By way of non-limiting example, closure element 114 may be formed of a resilient or superelastic material that may be selectively deformed through the application of force and then return to a natural or predefined shape when the force is removed.

Forming closure element 114 of a resilient or superelastic material can simplify the procedure for moving foot and needle guide portions 116, 118 from the deployed configuration to the delivery configuration. For instance, closure element 114 may have a natural or predefined shape similar to that shown in FIG. 1. Closure element 114 may be deployed in a manner similar to that described herein (i.e., moving handles 120, 122 proximally). That is, a force or forces may be applied to foot portion 116 and needle guide portion 118 to cause axially compression and radially expansion as described herein. However, rather than having to apply a force or forces (i.e., moving handles 120, 122 distally) to move foot and needle guide portions 116, 118 back to the delivery configuration, the resilient or superelastic nature of closure element 114 can automatically return foot and needle guide portions 116, 118 back to the delivery configuration when the original force(s) are removed. That is, after handles 120, 122 have been drawn proximally to deploy closure element 114, handles 120, 122 can simply be let go and the resilient or superelastic nature of closure element will cause foot and needle guide portions 116, 118 to return to the delivery configuration without requiring the user to affirmatively move handles 120, 122 distally.

In connection with forming closure element 114 of a resilient or superelastic material, rod 150 may be formed a non-rigid material, such as a thread, cable, rope, or the like. The non-rigid rod 150 would still be able to be pulled proximally to move foot portion 116 to the deployed configuration as discussed herein. However, there would no longer be a need to push on rod 150 to move foot portion 116 back to the delivery configuration since the resilient nature of foot portion 116 would automatically move foot portion 116 back to the delivery configuration once handle 120 is let go. As a result, rod 150 would not need to be rigid to push foot portion 116 back to the delivery configuration.

In still another exemplary embodiment, closure element 114 may be formed of a shape memory material and designed to be positioned within elongate member 106 and selectively extended out of distal end 110 of elongate member 106. As is understood by one of ordinary skill in the art, shape memory materials may be formed into a desired shape and heat-set so that the material "remembers" the desired shape. The material can then be bent, straightened, compacted, and placed into various contortions by the application of requisite forces; however, after the forces are released the shape memory material can be capable of returning to the memory shape.

With regard to closure element 114 being formed of a shape memory material, closure element 114 may be configured in the deployed configuration shown in FIGS. 2, 5, and 8-10 and then heat-set so that the material retains the deployed shape. Once closure element 114 has been heat-set in the deployed configuration shape, closure element 114 can be straightened into the delivery configuration shown in FIGS. 1 and 3 and inserted into elongate member 106.

Elongate member 106 can be designed to maintain closure element 114 in the delivery configuration while closure element 114 is positioned therein.

In use, elongate member 106 (with closure element 114 disposed therein) is inserted into the patient until distal end 110 of elongate member 106 is positioned adjacent the exterior surface of lumen wall 156 and across puncture 154. Once so positioned, closure element 114 can be extended out of elongate member 106, through puncture 154, and into the body lumen. As closure element 114 extends out of elongate member 106, closure element 114 will return to the memory shape (i.e., the deployed configuration shape). Thus, as foot portion 116 is extended out of elongate member 106 and into the body lumen, foot portion 116 will automatically move to the deployed configuration. Once foot portion 116 is positioned within the body lumen as desired, elongate member 106 may be withdrawn proximally to uncover needle guide portion 118. As needle guide portion 118 is uncovered, needle guide portion 118 will automatically move to the memory shape (i.e., the deployed configuration shape). Needles 144 can then be deployed and withdrawn as described above. After needles 144 have been withdrawn, closure element 114 can be retracted back into elongate member 106 and removed from the patient. More specifically, closure element 114 may be designed so that needle guide portion 118 and foot portion 116 collapse back to the delivery configuration as closure element 114 is pulled proximally against distal end 110 of elongate member.

While exemplary embodiments have been described herein with particular detail, including various combinations of particular aspects, features, structure, and functions, it will be appreciated that the present invention may include combinations other than those described in particular detail above. For instance, in one aspect of the disclosure, a device for closing an opening in tissue includes a body member having a proximal portion, a distal portion, and a waist portion located between the proximal portion and the distal portion.

In another aspect that may be combined with any of the aspects herein, the proximal portion and the distal portion each have a delivery configuration and a deployed configuration.

In another aspect that may be combined with any of the aspects herein, a plurality of proximal slits are disposed in the proximal portion of the body member.

In another aspect that may be combined with any of the aspects herein, the proximal slits cooperate with the body member to facilitate the proximal portion changing from the delivery configuration to the deployed configuration.

In another aspect that may be combined with any of the aspects herein, a plurality of distal slits are disposed in the distal portion of the body member.

In another aspect that may be combined with any of the aspects herein, the distal slits cooperate with the body member to facilitate the distal portion changing from the delivery configuration to the deployed configuration.

In another aspect that may be combined with any of the aspects herein, a plurality of needle guide apertures are formed in the proximal portion and are adapted to have at least one needle pass therethrough.

In another aspect that may be combined with any of the aspects herein, at least one cuff is removably mounted in the distal portion.

In another aspect that may be combined with any of the aspects herein, the delivery configurations have smaller cross-sectional sizes than the deployed configurations.

In another aspect that may be combined with any of the aspects herein, the device also includes a first actuator operatively associated with the body member to cause the distal portion to change between the delivery configuration and the deployed configuration.

In another aspect that may be combined with any of the aspects herein, the first actuator comprises a rod connected to the distal end of the body member.

In another aspect that may be combined with any of the aspects herein, the rod has a handle disposed at a proximal end of the device.

In another aspect that may be combined with any of the aspects herein, the device also includes a second actuator operatively associated with the body member to cause the proximal portion to change between the delivery configuration and the deployed configuration.

In another aspect that may be combined with any of the aspects herein, the second actuator comprises a rod connected to the waist portion of the body member.

In another aspect that may be combined with any of the aspects herein, the rod has a handle disposed at a proximal end of the device.

In another aspect that may be combined with any of the aspects herein, the proximal and distal portions each change from the delivery configuration to the deployed configuration by axially compressing and radially expanding.

In another aspect that may be combined with any of the aspects herein, the plurality of needle guide apertures and the at least one cuff are aligned with one another.

In another aspect that may be combined with any of the aspects herein, the at least one cuff comprises two cuffs.

In another aspect that may be combined with any of the aspects herein, a length of suture is connected between the two cuffs.

In another aspect that may be combined with any of the aspects herein, a device for closing an opening in a body lumen includes an elongate member having a proximal end, a distal end, a central passage and at least one needle lumen extending from the proximal end toward the distal end.

In another aspect that may be combined with any of the aspects herein, at least one needle is disposed within and advanceable from the at least one needle lumen.

In another aspect that may be combined with any of the aspects herein, a closure element extends from the distal end of the elongate member.

In another aspect that may be combined with any of the aspects herein, the closure element has a proximal portion, a distal portion, and a waist portion.

In another aspect that may be combined with any of the aspects herein, the proximal portion and the distal portion are each configured to move between a delivery configuration and a deployed configuration.

In another aspect that may be combined with any of the aspects herein, the proximal portion comprises a plurality of needle guide apertures and the distal portion has at least one cuff removably mounted therein.

In another aspect that may be combined with any of the aspects herein, the plurality of needle guide apertures guide the at least one needle to the at least one cuff when the proximal and distal portions are in the deployed configurations and as the at least one needle is advanced from the at least one needle lumen.

In another aspect that may be combined with any of the aspects herein, the closure element further comprises a plurality of proximal slits and a plurality of distal slits that facilitate the movement of the proximal portion and the distal portion between the delivery configuration and the deployed configuration.

In another aspect that may be combined with any of the aspects herein, the distal portion and the proximal portion are independently movable between the delivery configurations and the deployed configurations.

In another aspect that may be combined with any of the aspects herein, the at least one cuff is disposed radially further away from a longitudinal axis of the device than the plurality of needle guide apertures when the proximal and distal portions are in the deployed configurations.

In another aspect that may be combined with any of the aspects herein, the plurality of needle guide apertures comprises at least one proximal needle guide aperture and at least one distal needle guide aperture.

In another aspect that may be combined with any of the aspects herein, the at least one distal needle guide aperture is disposed radially further away from a longitudinal axis of the device than the at least one proximal needle guide aperture when the proximal and distal portions are in the deployed configurations.

In another aspect that may be combined with any of the aspects herein, a closure device for use in closing an opening in a wall of a body lumen includes an elongate member having at least one pair of needle lumens extending therethrough.

In another aspect that may be combined with any of the aspects herein, at least one pair of needles are disposed in the at least one pair of needle lumens.

In another aspect that may be combined with any of the aspects herein, the at least one pair of needles are selectively advanceable from the at least one pair of needle lumens.

In another aspect that may be combined with any of the aspects herein, a closure element has a longitudinal axis and includes a foot portion and a needle guide portion.

In another aspect that may be combined with any of the aspects herein, the foot portion has a delivery configuration and a deployed configuration.

In another aspect that may be combined with any of the aspects herein, the foot portion is configured to pass through the opening in the wall of the body lumen when in the delivery configuration and resist passage through the opening in the wall of the body lumen when in the deployed configuration.

In another aspect that may be combined with any of the aspects herein, the foot portion has at least one pair of cuffs removably mounted thereon.

In another aspect that may be combined with any of the aspects herein, a length of suture is connected between the at least one pair of cuffs.

In another aspect that may be combined with any of the aspects herein, the needle guide portion has a delivery configuration and a deployed configuration.

In another aspect that may be combined with any of the aspects herein, the needle guide portion has at least one pair of proximal needle guide apertures and at least one pair of distal needle guide apertures.

In another aspect that may be combined with any of the aspects herein, the proximal and distal needle guide apertures guide the at least one pair of needles toward the at least one pair of cuffs when the needle guide portion is in the deployed configuration and as the at least one pair of needles are advanced from the at least one pair of needle lumens.

In another aspect that may be combined with any of the aspects herein, the at least one pair of needles is adapted to securely engage the at least one pair of cuffs.

In another aspect that may be combined with any of the aspects herein, the at least one pair of needles and the least at least one pair of cuffs are adapted to be withdrawn together to pull the length of suture through the wall of the body lumen.

In another aspect that may be combined with any of the aspects herein, the foot portion is adapted to be used as a locator when positioned within the body lumen and moved to the deployed configuration.

In another aspect that may be combined with any of the aspects herein, the device also includes a first actuator and a second actuator.

In another aspect that may be combined with any of the aspects herein, the first actuator is adapted to move the needle guide portion between the delivery and deployed configurations.

In another aspect that may be combined with any of the aspects herein, the first and second actuators are adapted to cooperatively move the foot portion between the delivery and deployed configurations.

In another aspect that may be combined with any of the aspects herein, the device includes a first plurality of slits disposed within the foot portion.

In another aspect that may be combined with any of the aspects herein, the device also includes a second plurality of slits disposed within the needle guide portion.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. It shall be further understood that although the present invention has been described in relation to vessel closure, it is contemplated that the closure component of the present invention may be utilized to close other openings in the body such as PFO openings, or openings formed in organs such as the stomach for certain surgical procedures.

What is claimed is:

1. A method of closing an opening in tissue, the method comprising:
    positioning a member relative to the opening in tissue, the member being movable from a delivery configuration to a deployed configuration where a portion of the member aids in locating tissue, the member comprising a first member, a second member, and a bend portion between the first member and the second member, the first member and the second member generally overlapping each other when viewed in a proximal to distal direction in the deployed configuration, each of the first member and the second member comprising an opening; and
    withdrawing a needle through tissue adjacent to the opening to withdraw a suture attached to an end of the needle through the tissue, before the needle is withdrawn through the tissue the needle extends through the opening in the first member and the opening in the second member with the end of the needle being disposed distal the second member and another end of the needle being disposed proximal the first member.

2. The method of claim 1, wherein the delivery configuration has a smaller cross-sectional size than the deployed configuration.

3. The method of claim 1, wherein withdrawing the needle further comprises proximally advancing the needle into an elongate member coupled to a proximal handle.

4. The method of claim 3, further comprising withdrawing the needle through a needle access opening in the elongate member.

5. The method of claim 1, wherein withdrawing the needle to withdraw the suture further comprises withdrawing the suture from a suture support structure distal the member.

6. The method of claim 5, wherein the suture support structure comprises a suture receiving opening through which the suture distally extends.

7. The method of claim 1, further comprising moving the member relative to an elongate member proximal the member to transition the member from the delivery configuration to the deployed configuration.

8. A method of closing an opening in tissue, the method comprising:
    positioning a member relative to the opening in tissue, the member being movable from a delivery configuration to a deployed configuration where a portion of the member aids in locating tissue, the member being disposed distal an elongate member coupled to a proximal handle, the member comprising a first member, a second member, and a hinge portion between the first member and the second member, the first member and the second member generally overlapping each other when viewed along a longitudinal axis of the elongate member in the deployed configuration, each of the first member and the second member comprising an opening; and
    withdrawing a needle through tissue adjacent to the opening to withdraw a suture attached to an end of the needle through the tissue, before the needle is withdrawn through the tissue the needle extends through the opening in the first member and the opening in the second member with the end of the needle being disposed distal the second member and another end of the needle being disposed proximal the first member.

9. The method of claim 8, wherein positioning the member from the delivery configuration to the deployed configuration comprises moving the member relative to the elongate member to radially expand the member from the delivery configuration to the deployed configuration.

10. The method of claim 8, further comprising withdrawing the needle through a needle access opening in the elongate member.

11. The method of claim 8, wherein withdrawing the needle to withdraw the suture further comprises withdrawing the suture from a suture support structure distal the member.

12. The method of claim 11, wherein the suture support structure comprises a suture receiving opening through which the suture distally extends.

13. A method of closing an opening in tissue, the method comprising:
    positioning a tissue locating member through the opening, the tissue locating member being disposed distal an elongate member and proximal a suture receiving opening, the member comprising a first member, a second member, and a hinge portion disposed between the first member and the second member;
    transitioning the first member and the second member from a delivery configuration to a deployed configuration, the first member and the second member moving longitudinally and radially as the first member and the second member transition from the delivery configuration to the deployed configuration; and
    withdrawing a needle through tissue adjacent to the opening to withdraw a suture attached to an end of the needle through the tissue, before the needle is withdrawn through the tissue the needle extends through an opening in the first member and an opening in the second member with an end of the needle being disposed distal the second member and another end of the needle being disposed proximal the first member with the suture being received by a suture receiving opening.

14. The method of claim 13, wherein the first member, the second member, and the hinge portion form a generally V-shaped structure, when viewed in a direction transverse to a longitudinal axis of the elongate member, in the deployed configuration.

15. The method of claim 14, wherein withdrawing the needle further comprises proximally advancing the needle into the elongate member coupled to a proximal handle.

16. The method of claim 15, further comprising proximally advancing the needle through a needle access opening in the elongate member.

17. The method of claim 16, wherein withdrawing the needle to withdraw the suture further comprises withdrawing the suture from the suture receiving opening distal the member.

18. The method of claim 17, wherein withdrawing the suture from the suture receiving opening comprises releasing the suture from within the suture receiving opening.

19. The method of claim 18, further comprising moving the member relative to the elongate member proximal the member to transition the member from the delivery configuration to the deployed configuration.

* * * * *